(12) United States Patent
Sperling et al.

(10) Patent No.: US 10,775,374 B2
(45) Date of Patent: Sep. 15, 2020

(54) STATIONARY PHASE FOR DETECTING A SPECIFIC ANALYTE IN A MIXTURE, USES THEREOF AND METHOD FOR DETECTING A SPECIFIC ANALYTE IN A MIXTURE

(71) Applicant: FRAUNHOFER-GESELLSCHAFT ZUR FÖRDERUNG DER ANGEWANDTEN FORSCHUNG E.V., Munich (DE)

(72) Inventors: Ralph Sperling, Eltville (DE); Ralf Himmelreich, Mainz (DE); Tobias Schunck, Mainz (DE); Raphael Thiermann, Wiesbaden (DE)

(73) Assignee: Fraunhofer-Gesellschaft zur förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 16/348,013

(22) PCT Filed: Nov. 7, 2017

(86) PCT No.: PCT/EP2017/078492
§ 371 (c)(1),
(2) Date: May 7, 2019

(87) PCT Pub. No.: WO2018/087093
PCT Pub. Date: May 17, 2018

(65) Prior Publication Data
US 2019/0285628 A1    Sep. 19, 2019

(30) Foreign Application Priority Data
Nov. 8, 2016 (DE) .......... 10 2016 221 875

(51) Int. Cl.
*G01N 33/558* (2006.01)

(52) U.S. Cl.
CPC ................ *G01N 33/558* (2013.01)

(58) Field of Classification Search
None
See application file for complete search history.

(56) References Cited

U.S. PATENT DOCUMENTS

2013/0210028 A1    8/2013    Pache et al.

FOREIGN PATENT DOCUMENTS

| CN | 101 519 696 A | 9/2009 |
| DE | 102014203266 A1 | 8/2015 |

OTHER PUBLICATIONS

Bruno, John G., Application of DNA Aptamers and Quantum Dots to Lateral Flow Test Strips for Detection of Foodborne Pathogens with Improved Sensitivity versus Colloidal Gold, Pathogens, 3, pp. 341-355, available online Apr. 10, 2014. (Year: 2014).*

(Continued)

*Primary Examiner* — Rebecca M Giere
(74) *Attorney, Agent, or Firm* — Leydig, Voit & Mayer, Ltd.

(57) ABSTRACT

The invention presents a stationary phase for detecting at least one specific analyte in a mixture. The stationary phase includes a solid phase divided into a plurality of zones for transporting liquid by capillary force. The solid phase includes at least one first zone suitable for receiving a liquid sample, a second zone on which a receptor is immobilized, wherein the receptor is suitable for binding to a ligand, and a third zone on which quantum dots are immobilized, function as FRET donors and are linked to at least one suitable FRET acceptor via at least one oligonucleotide linker. The stationary phase exhibits improved detection sensitivity and allows simultaneous and multiparametric detection of a wide variety of analytes. The invention proposes uses of the stationary phase and also presents a (Continued)

Figure 1:
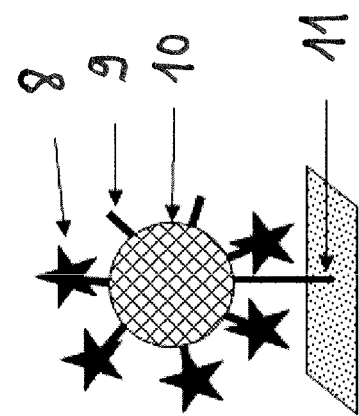
Figure 1:
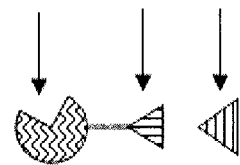
Figure 1:
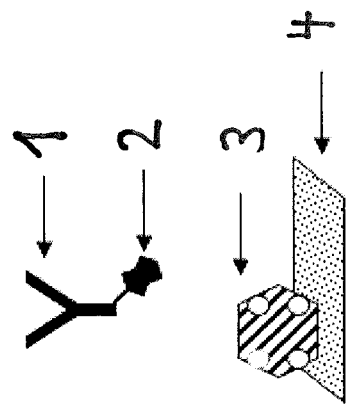

method for detecting at least one specific analyte in a mixture.

17 Claims, 4 Drawing Sheets

(56)  References Cited

OTHER PUBLICATIONS

Chen et al., "Micrococcal nuclease detection based on peptide-bridged energy transfer between quantum dots and dye-labeled DNA" *Talanta 97*: 533-538 (2012).
Huang et al., "A high sensitive and specific QDs FRET bioprobe for MNase," *Chem. Commun.*, pp. 5990-5992 (2008).
Huang et al., "A high sensitive and specific QDs FRET bioprobe for MNase," Supplemental Material/Support Information *Chem. Commun.*, 7 pgs. (2008).
European Patent Office, International Search Report in International Application No. PCT/EP2017/078492 (dated Feb. 7, 2018).
European Patent Office, Written Opinion in International Application No. PCT/EP2017/078492 (dated Feb. 7, 2018).
International Bureau of WIPO, International Preliminary Report on Patentability in International Application No. PCT/EP2017/078492 (dated May 14, 2019).
German Patent Office, Office Action in German Patent Application No. 10 2016 221 875.1 (dated Aug. 23, 2017).
German Patent Office, Decision to Grant in German Patent Application No. 10 2016 221 875.1 (dated Apr. 25, 2018) (includes listing of allowed claims).
German Patent Office, Corrected Decision to Grant in German Patent Application No. 10 2016 221 875.1 (dated May 3, 2018).

\* cited by examiner

STATIONARY PHASE FOR DETECTING A SPECIFIC ANALYTE IN A MIXTURE, USES THEREOF AND METHOD FOR DETECTING A SPECIFIC ANALYTE IN A MIXTURE

CROSS-REFERENCE TO RELATED APPLICATIONS

This patent application is the U.S. national phase of International Application No. PCT/EP2017/078492, filed on Nov. 7, 2017, which claims the benefit of German Patent Application No. 102016221875.1, filed Nov. 8, 2016, the disclosures of which are incorporated herein by reference in their entireties for all purposes.

A stationary phase for detecting at least one specific analyte in a mixture is presented. The stationary phase includes a solid phase divided into a plurality of zones for the transport of liquid by capillary force. The solid phase includes at least one first zone that is suitable for receiving a liquid sample, a second zone on which a receptor is immobilized, with the receptor being suitable for the binding of a ligand, and a third zone on which quantum dots are immobilized that act as a FRET donor and are connected to at least one suitable FRET acceptor via at least one oligonucleotide linker. The stationary phase has an improved detection sensitivity and permits a simultaneous and multiparametric detection of the most varied analytes. Uses of the stationary phase are proposed and a method is furthermore presented for detecting at least one specific analyte in a mixture.

Stationary phases, for example those of lateral flow strips, have already been known for decades. The problem with known stationary phases of lateral flow strips is that they are not sensitive enough for the detection of some analytes. To overcome this disadvantage, attempts have inter alia been made to replace the gold nanoparticles included as reporter particles in these stationary phases with other kinds of particle. It is known to use so-called "quantum dots" (abbreviated to "QD"), "nanophosphors", carbon nanoparticles and/or magnetic particles instead of the gold nanoparticles.

Quantum dots are fluorescent colloidal particles that comprise inorganic semiconductor materials. The fluorescent properties result from the band gap of the material and from the particle size in the range of a few nanometers ("quantum confinement effect"). To keep them stable in their liquid carrier medium, the surface of the QDs is as a rule coated with a layer of organic molecules that provides steric or electrostatic repulsion. Further molecules, in particular biomolecules, can be coupled chemically covalently to the QDs through different strategies or can be bound to the inorganic surface of the QDs by chemisorption and can displace the originally present stabilizer molecules in so doing. The QDs in this manner do not only serve as optically active species, but also serve as carrier particles for further (bio)molecular species or functions.

Fluorescence resonance energy transfer, also Förster resonance energy transfer (abbreviated to "FRET"), designates a nonradiative energy transfer from one excited species (FRET donor, e.g. a fluorescent molecule or QD) to another (FRET acceptor). On this energy transfer, the acceptor in turn moves into an excited state from which it may emit a photon (fluorescence) while the donor leaves its excited state without having emitted a photon (quenching). A spectral overlap between the donor emission and the acceptor absorption as well as a spatial proximity between the donor and the acceptor are required for such a resonant transfer process. The efficiency of the transfer drops with the sixth power of the distance so that molecular conformation changes can inter alia be observed with this process, which can be used in a variety of manners for biological detection reactions.

In addition to changing the reporter particles, attempts have been made to use a different detection process to increase the detection sensitivity of lateral flow strips. In the original stationary phases of the lateral flow strips, the molecular boding event was still simply visually read off. Fluorescence detectors and resonance coil magnetometers were later used for this purpose.

In addition to changing the kind of particles and the detection process, it is known in the prior art to increase the detection sensitivity by the use of enzymes that catalyze the formation of a dyestuff.

Starting from this, it was the object of the present invention to provide a stationary phase (e.g. for lateral flow strips) for detecting a specific analyte in a mixture that permits a high detection sensitivity and an multiparametric detection of a plurality of analytes simultaneously, i.e. in one application step.

The object is achieved by the disclosed stationary phase, by the disclosed kit, by the disclosed method, and by the disclosed use, as well as embodiments thereof.

A stationary phase for detecting a specific analyte in a mixture is presented in accordance with the invention. The stationary phase includes a solid phase divided into a plurality of zones for the transport of liquid by capillary force, with the solid phase at least a) including a first zone that is suitable for receiving a liquid sample;
b) including a second zone on which a receptor for binding an antibody and/or an aptamer is immobilized; and
c) including a third zone on which quantum dots are immobilized as FRET donors, with the quantum dots each being linked to at least one FRET acceptor via at least one oligonucleotide linker.

The stationary phase in accordance with the invention permits the binding of an antibody and/or of an aptamer for the specific binding of the specific analyte to be detected. A reaction solution can now be used for detecting a specific analyte in a mixture that includes stoichiometric complexes of antibody/aptamer and an analyte-nuclease conjugate. An analyte-nuclease conjugate is also understood as such conjugates in which the nuclease is bound—optionally via a spacer—to a molecule that substantially has the structure of the analyte, with this meaning that the analyte to be determined is suitable to dissociate the complex of antibody/aptamer and the analyte-nuclease conjugate. If a test sample that includes the specific analyte (=liquid sample) is now admixed to this reaction solution, the free liquid analyte dissociates the complex of antibody/aptamer and the analyte-nuclease conjugate (competitive displacement reaction).

In other words, a quantity of analyte-nuclease conjugate proportional to the quantity of specific analyte in the test sample is released and is no longer bound to the antibody or the aptamer. This quantity of specific analyte is consequently also not bound to the second zone when the liquid sample flows from the first zone to the second zone. This quantity of specific analyte consequently reaches the third zone in which the nuclease bound to the analyte cuts the oligonucleotide linker between the FRET donor and the FRET acceptor and thus destroys the FRET effect. The detection of the presence of the specific analyte to be detected is consequently successful with the aid of the stationary phase in accordance with the invention and of FRET spectroscopy.

It is further emphasized that the nuclease-catalyzed cleaving of the oligonucleotide linker effects an enzymatic amplification of the detection signal and thus a high detection sensitivity.

In addition, the stationary phase in accordance with the invention can be provided inexpensively.

The possibility of a multiparametric detection furthermore results. In the case of a self-fluorescent FRET acceptor, the emitted radiation is displaced in the case of a positive signal from a higher to a lower wavelength (blue shift of the fluorescence by the elimination of the FRET effect). In the case of a pure quencher, i.e. a non-emitting quencher, as the FRET acceptor, no blue shift can be observed, but only an increase in the fluorescence in the range of the emission wavelength of the FRET donor. The use of an emitting fluorescence dyestuff is of advantage here since the ratio of donor to acceptor concentration can be directly determined by a ratiometric detection, which enables a more robust quantitative detection.

In an advantageous embodiment, the quantum dots are respectively linked to a plurality of FRET acceptors, preferably at least two, particularly preferably at least five, and in particular at least ten (preferably identical) FRET acceptors via a plurality of oligonucleotide linkers. A higher number of FRET acceptors per individual quantum dot has the advantage that the signal strength increases (higher sensitivity) and the signal-to-noise ratio improves.

The solid phase for the transport of liquid by capillary force is preferably a solid phase for the transport of an aqueous liquid by capillary force. In this case, a capillary ascension in the direction of transport is effected by the use of an aqueous liquid (as a mobile phase). The solid phase particularly preferably has wetting properties that improve a transport of the liquid phase (e.g. of an aqueous liquid) by capillary forces. They are preferably hydrophilic properties in the case of an aqueous liquid. The solid phase (e.g. the solid phase of a lateral flow strip) can, however, have hydrophobic properties (e.g. hydrophobic regions) at least regionally to avoid a transport of an aqueous liquid in a direction of transport in at least one different direction than the direction of transport. It is thus conceivable, for example, that the solid phase includes strip-like hydrophobic regions (e.g. via a strip-like wetting of the solid phase with a hydrophobic substance (such as wax) at least regionally in parallel with the direction of transport. These strip-like hydrophobic regions represent a barrier for the aqueous liquid and thus enable a transport of the aqueous liquid in a plurality of mutually separate paths along the direction of transport.

In a preferred embodiment, the solid phase includes a plurality of contacting particles and/or fibers or consists thereof. The particles and/or fibers can here form intermediate spaces that have a maximum extent in all spatial directions of less than 1 mm, preferably less than 100 µm, particularly preferably less than 10 µm.

In a further preferred embodiment, the solid phase is selected from the group consisting of a solid phase of a lateral flow strip, a solid phase in a chamber and/or in a passage (e.g. a capillary, a tube and/or a column) of a microfluidic chip, a solid phase of a chromatography column, and combinations hereof. The dimensions of the chamber and/or of the passage of the microfluidic chip in a direction perpendicular to the direction of transport preferably amount to less than 10 mm, particularly preferably less than 1 mm, in particular less than 100 µm. The solid phase is particularly preferably the solid phase of a lateral flow strip.

The solid phase can comprise or consist of
i) inorganic particles and/or an inorganic fiber, preferably selected from the group consisting of alumina, glass fiber, mineral wool fiber, rock wool fiber, and mixtures thereof; and/or
ii) organic particles and/or an organic fiber, preferably selected from the group consisting of polymer particles, polymer fibers, and mixtures thereof, particularly preferably cellulose, cellulose acetate, nitrocellulose, polyvinylidene fluoride, nylon, nylon derivatives, polyethersulfone, carbon nanotubes, and mixtures thereof.

The first zone of the solid phase can
i) be arranged at a first end of the stationary phase, with the transport of liquid by capillary force optionally being blocked in at least one direction, preferably in at least two directions perpendicular to one another, particularly preferably in at least three directions perpendicular to one another, at the surface of the first zone, in particular by at least one margin of the stationary phase and/or by a wall of an element contacting the first zone (e.g. the wall of a lateral flow strip, of a microfluidic chip and/or of a chromatography column); or
ii) be arranged between a first and a second end of the stationary phase, preferably at the center of the stationary phase, with the transport of the liquid by capillary force optionally being blocked in at least one direction, preferably in at least two directions at an angle of 180° to one another, at the surface of the first zone, in particular by at least one margin of the stationary phase and/or by a wall of an element contacting the first zone (e.g. the wall of a lateral flow strip, of a microfluidic chip and/or of a chromatography column).

The second zone of the solid phase can be arranged next to the first zone on the stationary phase, with the transport of the liquid by capillary force optionally being blocked in at least one direction, preferably in at least two directions at an angle of 180° to one another, at the surface of the second zone, in particular by at least one margin of the stationary phase and/or by a wall of an element contacting the second zone (e.g. the wall of a lateral flow strip, of a microfluidic chip and/or of a chromatography column).

The receptor immobilized on the second zone
i) can be chemically covalently bound to the solid phase; and/or
ii) can be bound to the solid phase via non-covalent bonds, preferably via non-covalent bonds selected from the group consisting of ionic bonds, hydrogen bridge bonds, van der Waals interactions, hydrophobic effect, chelate bonds, thiol-gold bonds, and combinations thereof, particularly preferably via non-covalent bonds selected from the group consisting of antigen-antibody binding, ligand-aptamer binding, biotin-streptavidin binding, His-Tag binding, Ni-NTA binding, and combinations thereof; and/or
iii) can comprise or consist of biotin or derivatives thereof; and/or
iv) can comprise or consist of streptavidin or derivatives thereof.

The third zone can
i) be arranged at a second end of the stationary phase, with the transport of liquid by capillary force optionally being blocked in at least one direction, preferably in at least two directions perpendicular to one another, particularly preferably in at least three directions perpendicular to one another, at the surface of the second zone, in particular by at least one margin of the stationary phase and/or by a wall of an element contacting the third zone (e.g. the wall of a lateral flow strip, of a microfluidic chip and/or of a chromatography column); or ii) be arranged between a first and a second end of the stationary phase, preferably at the center of the stationary phase, with the transport of the liquid by capillary force optionally being blocked in at least one direction, preferably in at least two directions at an angle of 180° to one another, at the surface of the first zone, in particular by at least one margin of the stationary phase and/or by a wall of an element contacting the third zone (e.g. the wall of a lateral flow strip, of a microfluidic chip and/or of a chromatography column).

In a preferred embodiment, the third zone is divided into a plurality of mutually spatially separated subzones and quantum dots are immobilized on every single one of these subzones as FRET donors that are linked to a respective at least one FRET acceptor by an oligonucleotide linker, with the oligonucleotide linker of each subzone having a cutting site for a specific endonuclease and with the cutting site specific to a specific endonuclease differing for all the subzones. The simultaneous detection of a plurality of the most varied analytes is made possible by this embodiment (e.g. via the coupling of the different analytes to be detected to different endonucleases, with each of the different endonucleases being specific to an cutting site that is only located in a specific subzone). This embodiment is also advantageous since in addition to the specific analyte, marker molecules (e.g. specific proteins of pathogenic and harmless bacteria) can be simultaneously detected and the marker molecules can thus serve as a kind of internal standard. In this embodiment, the multiparametric detection takes place with spatial resolution using the same fluorescent species. In another embodiment, the detection of different species can take place by spectral multiplexing, i.e. a separate FRET pair is associated with each analyte and can then be detected in a mixture by its distinguishable fluorescence emission.

The quantum dots can comprise or consist of a material that is selected from the group consisting of II-VI semiconductors, III-V semiconductors, elements of the 4th main group of the periodic system of elements, PbSe, mixtures thereof, and alloys thereof, preferably a material selected from the group consisting of HgTe, HgSe, HgS, CdTe, CdSe, ZnTe, ZnSe, ZnS, GaN, GaP, GaAs, GaSb, InN, InP, InAs, InSb, Ge, Si and PbSe, with the quantum dots in particular having a shape selected from the group consisting of a spherical shape, a rod shape, a branched shape, core-shell particles, and combinations thereof.

The oligonucleotide linker
a) can have a specific cutting site for a specific endonuclease; and/or
b) can have one or more anchor groups for immobilizing the oligonucleotide linker at the third zone, with the immobilization optionally taking place via non-covalent interactions and/or at least one chemically covalent bond; and/or
c) can have one or more anchor groups for immobilizing the oligonucleotide linker at the quantum dots, with the immobilization optionally taking place via non-covalent interactions and/or at least one chemically covalent bond; and/or
d) can have a first, second, third, and/or fourth single-strand oligonucleotide.

The first, a second, a third, and/or a fourth single-strand oligonucleotide can
i) have a length in the range of 5 to 100 base pairs; and/or
ii) have a specific cutting site for a specific endonuclease; and/or iii) have one or more anchor groups for immobilizing the oligonucleotide linker at the third zone, with the immobilization optionally taking place via non-covalent interactions and/or at least one chemically covalent bond; and/or
iv) have one or more anchor groups for immobilizing the oligonucleotide linker at the quantum dots, with the immobilization optionally taking place via non-covalent interactions and/or at least one chemically covalent bond; and/or
v) have bound the FRET acceptor, preferably with the third single-strand oligonucleotide having bound the FRET acceptor.

In a preferred embodiment, the second single-strand oligonucleotide is at least regionally hybridized with the first oligonucleotide, the third single-strand oligonucleotide is at least regionally hybridized with the second oligonucleotide and/or the fourth single-strand oligonucleotide is at least regionally hybridized with the third oligonucleotide.

The specific cutting site for a specific endonuclease can be localized at the first, second, third and/or fourth single-strand oligonucleotide. The same applies accordingly to the one or more anchor groups for immobilizing the quantum dots on the third zone and also to the FRET acceptor, with the FRET acceptor particularly preferably being linked to the third single-strand oligonucleotide.

The oligonucleotide linker can comprise or consist of a oligonucleotide that is selected from the group consisting of DNA, RNA, PNA, LNA, CeNA, NP, tcDNA, xDNA, hybrids thereof, and mixtures thereof.

The solid phase can include a control enzyme zone that is preferably arranged between the first zone and the second zone, with a specific control endonuclease being immobilized on the control enzyme zone that is preferably bound to the solid phase via non-covalent interactions.

The solid phase can comprise a control oligonucleotide zone that is preferably arranged between the second zone and a suction zone for liquids, with a quantum dot being immobilized on the control oligonucleotide zone as a FRET donor that is linked to at least one FRET donor by at least one oligonucleotide linker, with the oligonucleotide linker preferably having a specific cutting site for a specific control endonuclease.

The solid phase can include a suction zone for liquids that is preferably arranged at a second end of the stationary phase, with the suction zone preferably comprising or consisting of a suction cushion ("suction pad").

The second zone, the control enzyme zone, the third zone and/or the control oligonucleotide zone can be arranged between a first and second end of the stationary phase, preferably in the order of second zone, control enzyme zone, third zone, and then control oligonucleotide zone, with the transport of the liquid by capillary force optionally being blocked in at least one direction, preferably in at least two directions at an angle of 180° to one another, at the surface of the zone, in particular by at least one margin of the stationary phase and/or by a wall of an element contacting the zone (or zones) (e.g. the wall of a lateral flow strip, of a microfluidic chip and/or of a chromatography column).

In accordance with the invention, a kit is furthermore provided for detecting a specific analyte in a mixture, comprising at least one stationary phase in accordance with the invention and a reaction solution, wherein the reaction solution
a) comprises a nuclease, with the nuclease being chemically bound to at least one specific analyte and/or to at least one molecule analog to the specific analyte; and b) comprises an antibody and/or an aptamer, with the antibody and/or the aptamer being suitable to bind the at least one specific analyte;

characterized in that the nuclease is completely present in a complex with the antibody and/or the aptamer.

The bond of the nuclease to the at least one specific analyte (or an analyte-analog molecule) can be via non-covalent chemical interactions (e.g. non-covalent bonds selected from the group consisting of ionic bonds, hydrogen bridge bonds, van der Waals interactions, hydrophobic effect, chelate bonds, thiol-gold bonds, and combinations thereof, preferably selected from the group consisting of antigen-antibody binding, ligand-aptamer binding, biotin-streptavidin binding, His-Tag binding, Ni-NTA binding, and combinations thereof) or can also be a chemically covalent bond. The bond is preferably a chemically covalent bond.

A method of detecting at least one specific analyte in a mixture is furthermore provided, said method comprising the steps a) providing a reaction solution including a nuclease that is chemically bound to at least one specific analyte and/or at least one molecule analog to the specific analyte and an antibody and/or an aptamer, with the antibody and/or the aptamer being suitable to bind the at least one specific analyte, and with the nuclease being completely present in a complex with the antibody and/or with the aptamer;
b) mixing the reaction solution with a mixture that could include the at least one specific analyte;
c) contacting the incubated reaction solution with the first zone of the solid phase of the stationary phase in accordance with one of the preceding claims;
d) measuring a FRET signal in at least one partial region of the third zone by FRET spectroscopy before the reaction solution has reached the third zone of the stationary phase;
e) measuring a FRET signal in at least one partial region of the third zone by FRET spectroscopy after the reaction solution has reached the third zone of the stationary phase;
f) comparing the FRET signals measured in step d) and step e); and
g) determining the presence of the specific analyte in the mixture with reference to the difference determined in step f).

The comparison of the FRET signals measured in step d) and step e) in step f) can take place once at the end of the method (end point measurement) and/or can take place multiple times up to the end of the method, i.e. at different points in time to record the kinetics of the development of the FRET signal.

It also applies in the method that the bond of the nuclease to the at least one specific analyte (or an analyte-analog molecule) can be configured via non-covalent chemical interactions (e.g. non-covalent bonds selected from the group consisting of ionic bonds, hydrogen bridge bonds, van der Waals interactions, hydrophobic effect, chelate bonds, thiol-gold bonds, and combinations thereof, preferably selected from the group consisting of antigen-antibody binding, ligand-aptamer binding, biotin-streptavidin binding, His-Tag binding, Ni-NTA binding, and combinations thereof); or can also be configured as a chemically covalent bond. The bond is preferably a chemically covalent bond.

Finally, the use of a stationary phase in accordance with the invention is proposed for detecting at least one specific analyte in a mixture with the aid of FRET spectroscopy. The use for detecting at least one analyte is preferably selected from the group consisting of protein, DNA, RNA, organic molecule having a mass ≤500 Da, inorganic molecule, inorganic particles, cells, viruses, virus components, and combinations thereof, in particular bacterial toxins, antibiotics, bacterial cells, and combinations thereof.

The subject matter in accordance with the invention will be explained in more detail with reference to the following examples and Figures without intending to restrict it to the specific embodiments shown here.

REFERENCE NUMERAL LIST

1: antibody/aptamer
2: anchor group (e.g. biotin)
3: receptor (e.g. streptavidin)
4: second zone of the solid phase
5: nuclease (endonuclease or exonuclease)
6: analyte to be determined bound to nuclease or molecule analog thereto
7: free analyte to be determined
8: FRET acceptor
9: oligonucleotide linker
10: quantum dot (=FRET donor)
11: third zone of the solid phase
11: third zone of the solid phase with a plurality of subzones
12: reaction solution with nuclease-analyte antigen/aptamer complex
13: admixing of analyte(s) to be determined to the reaction solution
14: light emission with FRET (e.g. emission of red light)
15: light emission without FRET (e.g. emission of green light)
16: second analyte to be determined or molecule analog thereto
17: third analyte to be determined or molecule analog thereto
18: first zone of the solid phase for receiving a liquid sample
19: control oligonucleotide zone
20: suction zone (includes e.g. a suction pad)
21: control enzyme zone
22: contacting the incubated reaction solution with the first zone
23: anchor group for immobilizing the oligonucleotide linker
24: anchor group for anchorage at the third zone
25: first single-strand oligonucleotide of the oligonucleotide linker
26: second single-strand oligonucleotide of the oligonucleotide linker
27: third single-strand oligonucleotide of the oligonucleotide linker
28: first possible cutting site for nuclease
29: second possible cutting site for nuclease
30: cleaving the oligonucleotide linker by nuclease FIG. 1 shows an antibody 1 (or an aptamer) that is chemically bound (e.g. via a covalent bond) to an anchor group 2 (e.g. biotin). A receptor 3 (e.g. streptavidin) is further shown that is immobilized on the second zone 4 of the solid phase. FIG. 1 further shows a nuclease 5 (e.g. an endonuclease or an exonuclease) that is chemically bound (e.g. via a covalent bond) to the analyte 6 to be determined (or to a molecule analog to it). The analyte 7 to be freely determined is furthermore shown. Finally, FIG. 1 shows a quantum dot 10 (=FRET donor) immobilized at the third zone 11 of the solid phase, with the quantum dot 10 being chemically linked (e.g. via a covalent bond) via an oligonucleotide linker 9 to a FRET acceptor (e.g. to a fluorescence dyestuff). The reference numerals for the symbols shown in FIG. 1 equally apply to FIGS. 2 to 4.

Figure 2:
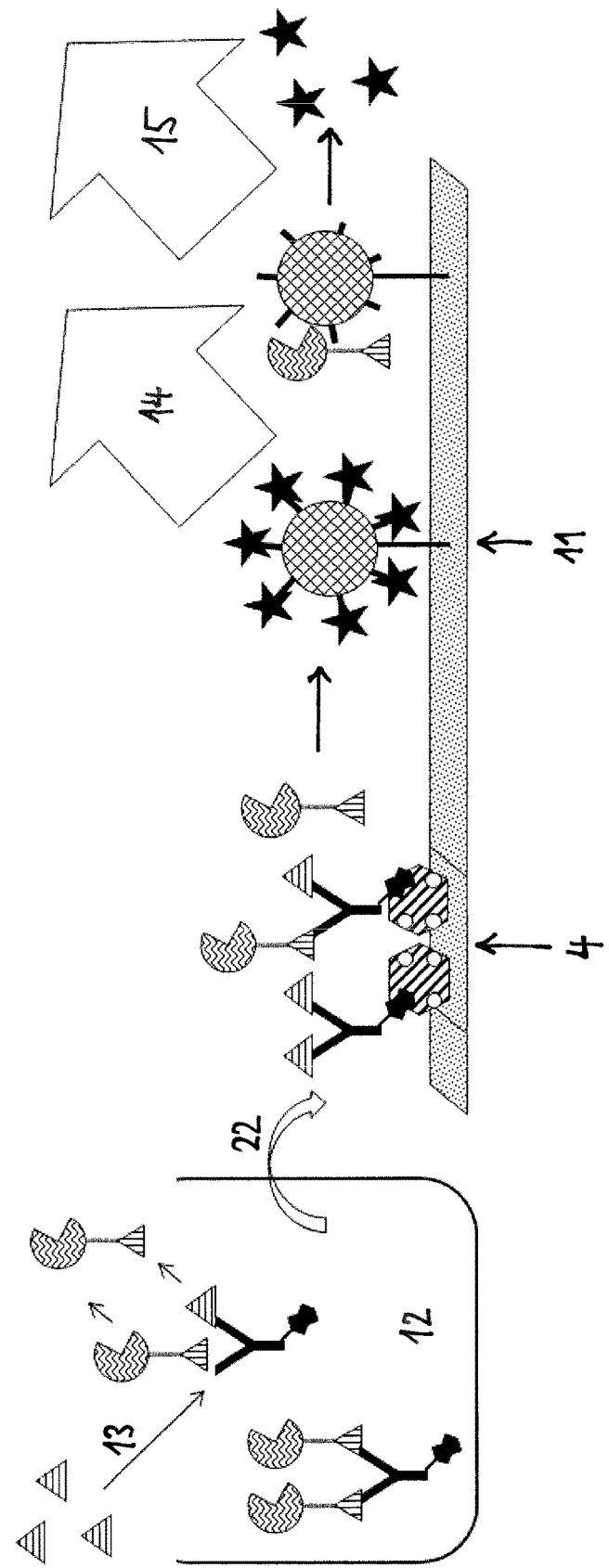

FIG. 2 schematically shows an embodiment of the method in accordance with the invention. An admixture 13 of analyte(s) to be determined takes place into the reaction solution 12 that includes a stoichiometric complex of nuclease analyte and the antibody/aptamer. After a specific incubation time, the reaction solution is applied 22 to the first zone of the solid phase of the stationary phase. The liquid reaction solution is transported along the stationary phase by capillary forces, with the molecules included in the reaction solution passing through the second zone 4 of the solid phase. All the antibodies/aptamers and molecules bound thereto are immobilized there so that only nuclease-analyte complexes not bound to antibodies/aptamers can reach the third zone 11 of the solid phase. They there impact the quantum dot (FRET donor) and the FRET acceptor that are linked to one another via the oligonucleotide linker and that show light emission 14 with FRET (e.g. emission of red light). The nuclease now cuts the oligonucleotide linker, whereby the spatial proximity between the FRET donor and the FRET acceptor is destroyed and FRET can no longer occur. A light emission 15 without FRET (e.g. emission of green light) consequently arises in the third zone of the solid phase. This change in the emission wavelength of the light can be spectroscopically measured.

Figure 3:
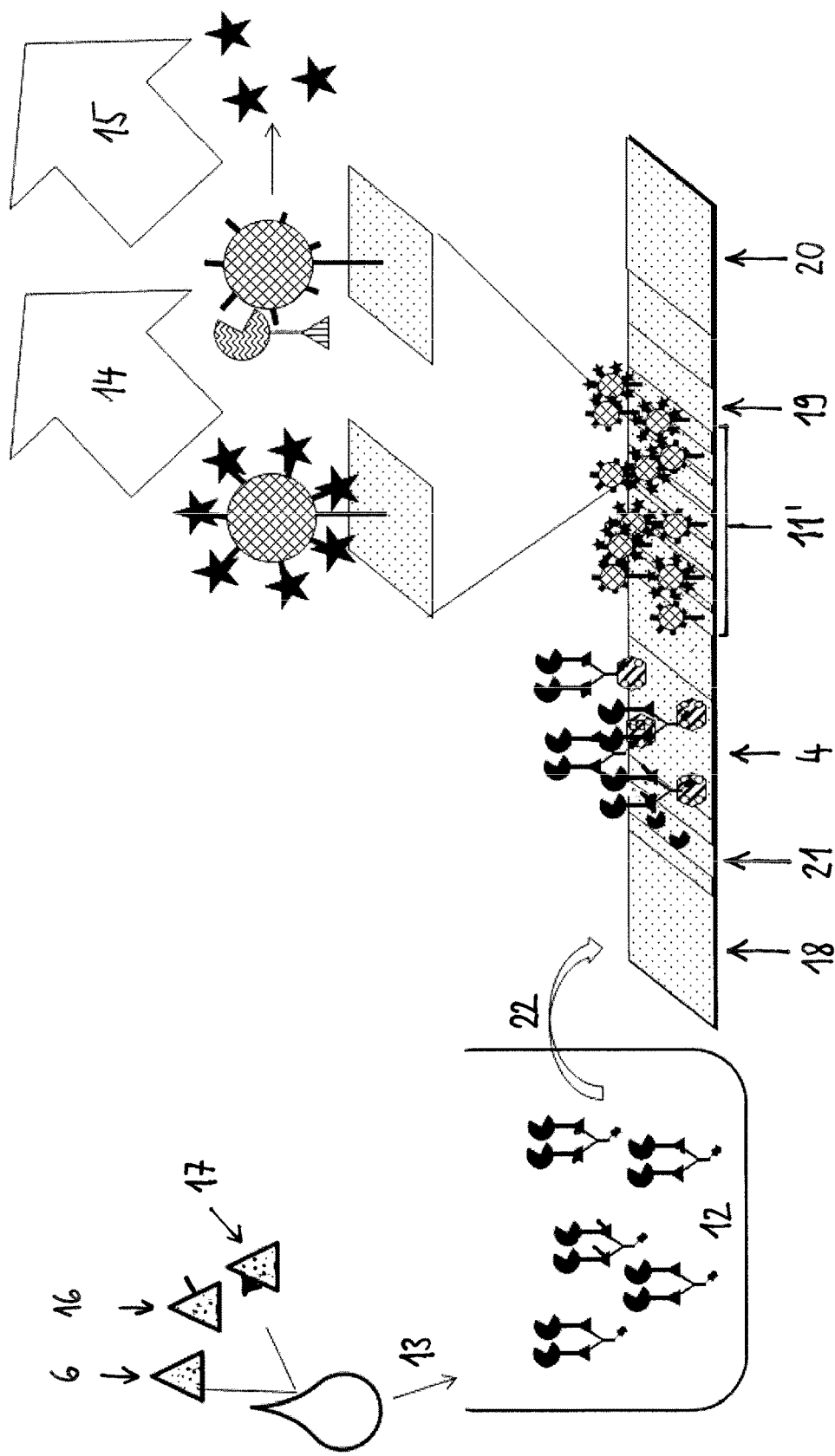

FIG. 3 shows a further embodiment of the method in accordance with the invention. Here, three different analytes 6, 16, 17 to be determined are admixed to the reaction solution 12, with the reaction solution including a corresponding stoichiometric complex of nuclease analyte and the antibody/aptamer for each of the analytes to be determined. After a specific incubation time, the reaction solution is applied 22 to the first zone 18 of the solid phase of the stationary phase. The liquid reaction solution is transported along the stationary phase by capillary forces, with the molecules contained in the reaction solution here first passing through a control enzyme zone 21 before they can reach the second zone 4 of the solid phase. In the second zone 4 of the solid phase, all the antibodies/aptamers and molecules bound thereto are immobilized so that only nuclease-analyte complexes not bound to antibodies/aptamers can reach the third zone 11' of the solid phase comprising a plurality of subzones in this embodiment. They there impact a respective specific pairing of quantum dot (FRET donor), FRET acceptor, and oligonucleotide linker in each of the subzones of the third zone 11'. It is, for example, sufficient for this purpose that each subzone has an oligonucleotide linker having a specific cutting site that can be cut either only by the nuclease of the first analyte 6, by the nuclease of the second analyte 16, or by the nuclease of the third analyte 17. If the specific nuclease of one of the specific analytes 6, 16, 17 impacts this subzone, the light emission 14 disappears with FRET (e.g. emission of red light) and a light emission 15 without FRET (e.g. emission of green light) occurs in this subzone. This change in the emission wavelength of the light can be read separately for each subzone of the third zone 11'. In this embodiment, the stationary phase additionally includes a control oligonucleotide zone 19 and a suction zone (e.g. includes a suction pad).

Figure 4:
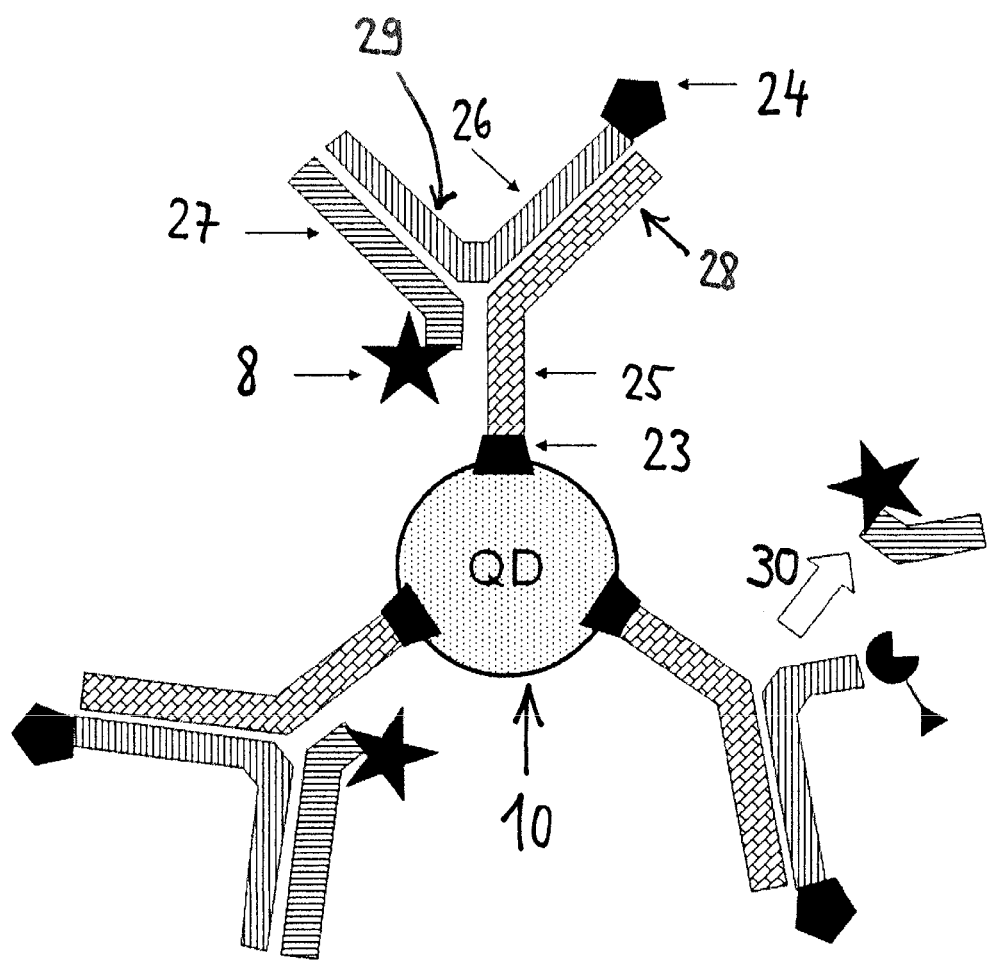

FIG. 4 shows a possible link of a quantum dot 10 (FRET donor) to a FRET acceptor 8 via an oligonucleotide linker. In this respect, a first single-strand oligonucleotide 25 of the oligonucleotide linker is bound to the quantum dot 10 via an anchor group 23 (e.g. a 6×His-Tag) (chelate bonding). The first single-strand oligonucleotide 25 is hybridized with a second single-strand oligonucleotide 26, with the second single-strand oligonucleotide 26 having an anchor group 24 for anchorage to the third zone. A first cutting site 28 for a nuclease can be encoded at the hybridization point of the first single-strand oligonucleotide 25 and of the second single-strand oligonucleotide 26. Furthermore, in this embodiment, a third single-strand oligonucleotide 27 is hybridized to the second single-strand oligonucleotide 26, with a second cutting site 29 for a nuclease optionally being able to be encoded here. The third single-strand oligonucleotide 27 carries the FRET acceptor 8 and moves it into direct spatial proximity with the quantum dot 10 (FRET donor). It is additionally shown in FIG. 4 how the structure looks after cleaving 30 of the oligonucleotide linker by the action of the nuclease. It becomes clear that the FRET acceptor 8 is no longer arranged in the direct vicinity of the quantum dot 10 (FRET donor) after the cleaving and that FRET can thus no longer occur.

EXAMPLE 1—EXAMPLE OF A METHOD IN ACCORDANCE WITH THE INVENTION FOR DETECTING AT LEAST ONE SPECIFIC ANALYTE IN A MIXTURE

A mixture that could include the sought analyte ("sample") is admixed with a reaction solution that includes biotin-modified antibodies and antigen-nuclease conjugates in a pre-incubation, with the antibodies being directed toward the antigen and at least one antigen corresponding to the sought analyte. All the antigen-nuclease conjugates of the reaction solution are present in an antibody-bound state (e.g. are complexed with the antibody). After admixing of the sample, a competitive binding reaction takes place: On the presence of an analyte in the sample that is structurally identical with the antigen, the antigen-nuclease conjugates bound to the antibody are partially displaced from the antibody and are now freely present in the reaction solution.

The reaction solution mixed with the mixture is subsequently applied to the first zone of the stationary phase. After the application to the first zone of the stationary phase, the released molecules migrate to the second zone of the stationary phase ("capture zone"), driven by capillary force—optionally via a control enzyme zone. A receptor (here: streptavidin) is immobilized on the second zone and is suitable for binding a biotinylated antibody (streptavidin-biotin bond). Consequently, all the biotinylated antibodies (and the antigen-nuclease conjugates bound to them) are bound via the biotin-streptavidin bond in the second zone and cannot move further in the direction of the third zone of the stationary phase.

Only the specific antigen-nuclease conjugates previously released by competitive interaction, i.e. those antigen-nuclease conjugates whose antigen is structurally analog to or identical with the analyte, are transported further to the third zone of the stationary phase ("detection zone") by capillary force. In the third zone, the antigen-nuclease conjugates impact quantum dots as the FRET donor that are immobilized on the third zone and are bound to a FRET acceptor via an oligonucleotide linker. The spatial proximity of the FRET donor and of the FRET acceptor provides that FRET takes place. If, however, the analyte-nuclease conjugate now impacts the third zone, the oligonucleotide linker is cleaved by the enzymatic effect of the nuclease. This has the effect that the spatial proximity between the FRET donor and the FRET acceptor is lost due to the Brownian molecular motion and the flow driven by capillary force. The FRET between the QD as the FRET donor and its FRET acceptor comes to a standstill which can be read as a positive signal via FRET spectroscopy. The signal is, for example, read via a lateral flow reader having imaging and spectrally resolved fluorescence detection. This can take place using a spectrometer, but also using two color filters.

Due to the catalytic character of the reaction, a nuclease molecule can effect a plurality of or a large number of cleaving reactions, whereby signal amplification occurs.

EXAMPLE 2—PREPARING AN OLIGONUCLEOTIDE LINKER IN ACCORDANCE WITH THE INVENTION

To keep the hybridization of single-strand oligonucleotides stable at room temperature (25° C.), approximately 10 to 20 complementary base pairs are required. If the oligonucleotide linker includes a specific cutting site of a restriction endonuclease, it is ideally at the center of the complementary base pairs. In the event that the restriction endonuclease cuts the oligonucleotide double strand with overhanging ends, the overhang may not be too long so as not to hybridize at room temperature after the cut. This requirement applies to a large part of all the known restriction endonucleases, however.

Design with Two Single-Strand Oligonucleotides ("II" Shape)

An oligonucleotide linker in accordance with the invention between the QD as the FRET donor and the FRET acceptor (e.g. a fluorescence dyestuff) can be built up of two single-strand oligonucleotides. The single-strand oligonucleotides are at least regionally hybridized with one another for this purpose. If the two oligonucleotides include a specific cutting site for a restriction endonuclease, it is located within the hybridized region.

Design with Three Single-Strand Oligonucleotides ("Y" Shape)

In this design, a first single strand oligonucleotide ("binding oligonucleotide") is first bound to the surface of a QD via an anchor group (e.g. via the 3' end of the oligonucleotide). The first single-strand oligonucleotide includes a spacer sequence S (e.g. at the 3' end) and a linker sequence L (e.g. at the 5' end). A second single-strand oligonucleotide ("linker oligonucleotide") is then hybridized via its linker sequence L' (e.g. at the 3' end of the second oligonucleotide) at the linker sequence L of the first single-strand oligonucleotide. The second single-strand oligonucleotide additionally has an cutting site sequence A (e.g. at the 5' end of the second oligonucleotide) that is specific to a specific restriction endonuclease. A third single-strand oligonucleotide ("reporter oligonucleotide") is then hybridized via its cutting site sequence A' (e.g. at the 3' end of the third oligonucleotide) at the cutting site sequence A of the second oligonucleotide. The third single-strand oligonucleotide has (e.g. in a chemically covalently bound manner) the FRET acceptor (e.g. a fluorescence dyestuff) (e.g. at the 5' end of the third oligonucleotide).

It is possible by the design via three single-strand oligonucleotides first only to prepare a kind of DNA-functionalized QD, namely a QD only modified by the binding oligonucleotide. Subsequently, a specificity of the oligonucleotide linker can be introduced for specific restriction endonucleases in a flexible manner by the addition of the linker oligonucleotide and of the reporter oligonucleotide. Due to the Y geometry of the oligonucleotide linker, the oligonucleotide sequence to be cut by the enzyme is sterically easily accessible and the dyestuff is as close as possible to the QD to enable a high FRET efficiency.

Design with Four Single-Strand Oligonucleotides (Immobilized "Y" Shape)

The modular concept for the design of the oligonucleotide linker simplifies the preparation and the optimization of the individual components and permits a whole series of possible variants. A further, fourth oligonucleotide can thus e.g. be attached to the binding oligo in addition to the linker oligo and is not cut by the nuclease and imparts the immobilization of the QD in the third zone on the solid phase of the stationary phase (e.g. via chemically covalent bonding of biotin to the fourth oligonucleotide when the solid phase of the third zone of the stationary phase has immobilized streptavidin).

Mixing of Oligonucleotides

In addition to the above-described linker oligonucleotides via which the FRET acceptor is bound to the surface of the QD, they can additionally be equipped with other oligonucleotides or other suitable molecules to obtain further functions (e.g. further chemical anchor groups, e.g. for the immobilization) or to increase the stability of the QD-FRET system. This means the colloidal stability and the stability on drying, storing and humidification during the detection reaction.

EXAMPLE 3—CONJUGATION OF A OLIGONUCLEOTIDE LINKER TO THE QD AND TO THE FRET ACCEPTOR

Quantum dots (QDs) are colloidal semiconductor nanoparticles having fluorescence properties. They are conjugated for the use in accordance with the invention via an oligonucleotide linker (preferably an oligonucleotide linker cleavable via sequence-specific nucleases) with a FRET acceptor (e.g. a fluorescence dyestuff molecule). The FRET acceptor is here selected in dependence on the type of the QD such that the fluorescence excitation of the QD is transferred to it via Förster resonance energy transfer (FRET). A fluorescence dyestuff molecule can be used as the FRET acceptor here that emits red light through the QD with FRET. Alternatively, a so-called "quencher" can be used as the FRET acceptor that does not emit itself, but that attenuates up to completely inhibits the intensity of the fluorescence emission of the QD. In this case, no emission intensity can be observed at the emission wavelength of the QD (e.g. green light) with FRET. The conjugation of the QDs to the FRET acceptor via the oligonucleotide linker preferably takes place in a chemically covalent manner.

Different analytes can be detected by the use of different oligonucleotide linkers. For this purpose, the analytes (antigens) to be detected are coupled to nucleases that only cut in a specific nucleotide sequence of the oligonucleotide linker (so-called restriction endonucleases). If the detection zone of the stationary phase comprises a plurality of subzones, every single subzone can have a specific oligonucleotide linker that can only be cut by a specific restriction endonuclease and a signal is thus only generated by this specific antigen-nuclease combination in the subzone. The sequence specific to the respective nuclease as a rule comprises approximately three base pairs; the cut can take place smoothly or offset depending on the enzyme selected. A plurality of analytes can be simultaneously detected by means of a spatially resolved (imaging) detection due to the use of the specific nucleases and specific cutting sites in the oligonucleotide linkers.

The invention claimed is:
1. A stationary phase for detecting a specific analyte in a mixture, comprising a solid phase divided into a plurality of separate zones for the transport of liquid by capillary force, wherein the solid phase at least includes
- a) a first zone that is suitable for receiving a liquid sample;
- b) a second zone on which a receptor for binding an antibody and/or an aptamer is immobilized, with the antibody and/or the aptamer being suitable to bind the at least one specific analyte; and
- c) a third zone on which quantum dots are immobilized as FRET donors, with the quantum dots each being linked to at least one FRET acceptor via at least one oligonucleotide linker, wherein the transport of liquid is in a direction from the first zone to the second zone and then to the third zone.

2. The stationary phase of claim 1, wherein the solid phase is selected from the group consisting of a solid phase of a lateral flow strip, a solid phase in a chamber and/or in a passage of a microfluidic chip, a solid phase of a chromatography column, and combinations thereof.

3. The stationary phase of claim 1, wherein the solid phase comprises:
- i) inorganic particles and/or an inorganic fiber; and/or
- ii) organic particles and/or an organic fiber.

4. The stationary phase of claim 1, wherein the first zone of the solid phase is arranged
- i) at a first end of the stationary phase, with the transport of liquid by capillary force optionally being blocked in at least one direction at the surface of the first zone; or
- ii) between a first and a second end of the stationary phase, with the transport of the liquid by capillary force optionally being blocked in at least one direction at the surface of the first zone.

5. The stationary phase of claim 1, wherein the second zone is arranged next to the first zone of the solid phase on the stationary phase, with the transport of the liquid by capillary force optionally being blocked in at least one direction at the surface of the second zone.

6. The stationary phase of claim 1, wherein the receptor immobilized on the second zone of the solid phase
- i) is chemically covalently bound to the solid phase; and/or
- ii) is bound to the solid phase via non-covalent bonds; and/or
- iii) comprises or consists of biotin or derivatives thereof; and/or
- iv) comprises or consists of streptavidin or derivatives thereof.

7. The stationary phase of claim 1, wherein the third zone of the solid phase is arranged
- i) at a second end of the stationary phase, with the transport of liquid by capillary force optionally being blocked in at least one direction, at the surface of the third zone; or
- ii) between a first and a second end of the stationary phase, with the transport of the liquid by capillary force optionally being blocked in at least one direction, at the surface of the first zone.

8. The stationary phase of claim 1, wherein the third zone is divided into a plurality of mutually spatially separated subzones and quantum dots are immobilized on every single one of these subzones as FRET donors that are linked to a respective at least one FRET acceptor by at least one oligonucleotide linker, with the oligonucleotide linker of each subzone having a specific cutting site for a specific endonuclease and with the cutting site specific to a specific endonuclease differing for all the subzones.

9. The stationary phase of claim 1, wherein the quantum dots comprise a material selected from the group consisting of II-VI semiconductors, III-V semiconductors, elements of the 4th main group of the periodic system of elements, PbSe, mixtures thereof, and alloys thereof.

10. The stationary phase of claim 1, wherein the oligonucleotide linker
- a) has a specific cutting site for a specific endonuclease; and/or
- b) has one or more anchor groups for immobilizing the oligonucleotide linker at the third zone, with the immobilization optionally taking place via non-covalent interactions and/or at least one chemically covalent bond; and/or
- c) has one or more anchor groups for immobilizing the oligonucleotide linker at the quantum dots, with the immobilization optionally taking place via non-covalent interactions and/or at least one chemically covalent bond; and/or
- d) has a first, second, third, and/or fourth single-strand oligonucleotide.

11. The stationary phase of claim 1, wherein the oligonucleotide linker comprises an oligonucleotide selected from the group consisting of DNA, RNA, PNA, LNA, CeNA, NP, tcDNA, xDNA, hybrids thereof, and mixtures thereof.

12. The stationary phase of claim 1, wherein the solid phase includes a control enzyme zone with a specific control endonuclease being immobilized on the control enzyme zone.

13. The stationary phase of claim 1, wherein the solid phase includes a suction zone for liquids.

14. The stationary phase of claim 1, wherein the solid phase includes a control oligonucleotide zone, with quantum dots being immobilized on the control oligonucleotide zone as a FRET donor that are linked to at least one FRET donor by at least one oligonucleotide linker.

15. The stationary phase of claim 1, wherein the second zone, a control enzyme zone, the third zone and/or a control oligonucleotide zone is/are arranged between a first and second end of the stationary phase, with the transport of the liquid by capillary force optionally being blocked in at least one direction at the surface of the zone.

16. A kit for detecting a specific analyte in a mixture, comprising at least one stationary phase in accordance with claim 1 and a reaction solution, wherein the reaction solution comprises
- a) a nuclease, with the nuclease being chemically bound to at least one specific analyte and/or to at least one molecule analog to the specific analyte; and
- b) an antibody and/or an aptamer, with the antibody and/or the aptamer being suitable to bind to the at least one specific analyte;

wherein the nuclease is completely present in a complex with the antibody and/or the aptamer.

17. A method of detecting at least one specific analyte in a mixture, the method comprising:
- a) providing a reaction solution comprising a nuclease that is chemically bound to at least one specific analyte and/or at least one molecule analog to the specific analyte, and an antibody and/or an aptamer, with the antibody and/or the aptamer being suitable to bind to the at least one specific analyte, and with the nuclease being completely present in a complex with the antibody and/or with the aptamer;
- b) mixing the reaction solution with a mixture that could include the at least one specific analyte;

c) contacting the incubated reaction solution with the first zone of the solid phase of the stationary phase of claim 1;
d) measuring a FRET signal in at least one partial region of the third zone by FRET spectroscopy before the reaction solution has reached the third zone of the stationary phase;
e) measuring a FRET signal in at least one partial region of the third zone by FRET spectroscopy after the reaction solution has reached the third zone of the stationary phase;
f) comparing the FRET signals measured in step d) and step e); and
g) determining the presence of the specific analyte in the mixture with reference to the difference determined in step f).

* * * * *